(12) United States Patent

Hung et al.

(10) Patent No.: US 9,005,912 B2
(45) Date of Patent: Apr. 14, 2015

(54) HYBRIDOMA CELL LINE FOR PRODUCING ANTIBODY FOR TYPE II COLLAGEN

(75) Inventors: Chih-Hsin Hung, Kaohsiung (TW);
Chi-Yen Shen, Kaohsiung (TW);
Shyh-Ming Kuo, Kaohsiung (TW);
I-Fen Chen, Kaohsiung (TW);
Shih-Han Wang, Kaohsiung (TW)

(73) Assignee: I-Shou University, Kaohsiung (TW)

( * ) Notice: Subject to any disclaimer, the term of this patent is extended or adjusted under 35 U.S.C. 154(b) by 395 days.

(21) Appl. No.: 13/562,123

(22) Filed: Jul. 30, 2012

(65) Prior Publication Data

US 2013/0309694 A1 Nov. 21, 2013

(30) Foreign Application Priority Data

May 17, 2012 (TW) .............................. 101117548 A

(51) Int. Cl.
 *C07K 16/18* (2006.01)
 *G01N 33/68* (2006.01)
 *G01N 33/543* (2006.01)
 *C07K 14/78* (2006.01)

(52) U.S. Cl.
 CPC ............ *C07K 16/18* (2013.01); *G01N 2333/78* (2013.01); *C07K 14/78* (2013.01); *G01N 33/543* (2013.01); *C07K 2317/34* (2013.01); *G01N 33/6887* (2013.01); *G01N 2800/105* (2013.01)

(58) Field of Classification Search
 None
 See application file for complete search history.

(56) References Cited

U.S. PATENT DOCUMENTS

| 6,132,976 | A | 10/2000 | Poole et al. |
| 6,642,007 | B1 | 11/2003 | Saltarelli et al. |
| 2011/0244482 | A1* | 10/2011 | Leeming et al. ............... 435/7.9 |
| 2012/0237948 | A1* | 9/2012 | Numata et al. ................. 435/7.4 |

\* cited by examiner

*Primary Examiner* — Christine Foster
(74) *Attorney, Agent, or Firm* — Muncy, Geissler, Olds & Lowe, P.C.

(57) ABSTRACT

The present invention provides a hybridoma cell line (DSM ACC3145), wherein the hybridoma cell line produces an antibody which specifically binds to an amino acid sequence of type II collagen comprising: K-G-E-P-G-D-D-G-P-S-C (as set forth in SEQ ID NO. 1); and a method for detecting osteoarthritis, by identifying a presence of type II collagen in a urine sample through containing the urine sample with the said antibody.

8 Claims, 3 Drawing Sheets

US 9,005,912 B2

HYBRIDOMA CELL LINE FOR PRODUCING ANTIBODY FOR TYPE II COLLAGEN

BACKGROUND OF THE INVENTION

1. Field of the Invention

The present invention relates to a hybridoma cell line, particularly to a hybridoma cell line which produces an antibody which specifically binds to a neopeptide of type II collagen and a method for detecting osteoarthritis by identifying a presence of type II collagen in a urine sample via the said antibody.

2. Description of the Related Art

Soft tissue of joint refers to tissues that connect, support, and surround bones, to cushion the friction between bones. There is a dynamic equilibrium between the synthesis and degradation of the molecules of the soft tissue of joint, for maintaining the said functions of the soft tissue of joint.

Degenerative arthritis, also known as osteoarthritis (OA), is a group of mechanical abnormalities involving degradation and deform of articular cartilage, and joint pain, tenderness or stiffness, caused by disequilibrium between the synthesis and degradation of the soft tissue of joint.

Conventional detections of osteoarthritis generally bases on identifying degraded fragments of soft tissues, such as collagen and proteoglycans in body fluids. The degraded fragments of soft tissues are present only when joints suffer from excessive pressures or friction. Due to the specificity of the degraded fragments of soft tissues, it is capable of being a biomarker of the detections of osteoarthritis. The conventional degraded fragments of soft tissues comprise CTXII, HELIX-II, C2C, coll2-1 and collagenase recognized site, including C2C1 and TII NE, and which have been widely used in screening people that is apt to have osteoarthritis.

A conventional method for detecting osteoarthritis comprises steps of identifying a presence of C2C fragment in blood samples or other body fluids, and detecting the blood samples or other body fluids with an antibody against C2C fragment. However, the titer and sensitivity of the antibody against C2C fragment is poor, only can being applied to samples that is collected via invasive procedures, blood and synovial fluid for example, since the C2C fragment has more than 20 amino acids, being easy to activate immune response in model animal and to prepare antibodies against thereof, but being inconvenient in practical use at home.

For improving the above conventional method, another conventional method for detecting osteoarthritis is disclosed in U.S. Pat. No. 6,642,007, entitled of "ASSAYS FOR MEASUREMENT OF TYPE II COLLAGEN FRAGMENTS IN URINE." The said conventional method for detecting osteoarthritis is carried by identifying a presence of type II collagen in urine sample with a complex of antibodies, comprising a capture antibody and a detection antibody against that against different epitopes on type II collagen neoepitope (TII NE), with the capture and detection antibodies both binding to target sequences, so that the sensitivity of the capture antibody can be promoted.

In specific, the said conventional method for detecting osteoarthritis is performed via sandwich enzyme linked immunosorbent assay, for improving the poor sensitivity of single antibody. However, the said conventional method for detecting osteoarthritis needs more resources, costs and times to develop various antibodies that against more than one epitope, and thus that, the diagnosis of osteoarthritis can not be achieved through an easy and low-cost process.

Hence there is a need of providing a user-friendly diagnostic method and apparatus for detecting osteoarthritis, which can provide an antibody that specifically binds to an epitope only comprising 10-15 amino acids from type II collagen, and does not bind to type I collagen or type III collagen.

SUMMARY OF THE INVENTION

The primary objective of this invention is to provide a hybridoma cell line, which produces an antibody that specifically binds to a neopeptide of type II collagen and is apt to detect osteoarthritis, achieving the detection of osteoarthritis through a convenient and low-cost process.

The secondary objective of this invention is to provide a method for detecting osteoarthritis, so that the detection of osteoarthritis is achieved through a simplified process by identifying the presence of type II collagen in a urine sample via an antibody that produces by the said hybridoma cell line.

A hybridoma cell line produces an antibody which specifically binds to a neopeptide of type II collagen comprising: K-G-E-P-G-D-D-G-P-S-C (as set forth in SEQ ID NO. 1), and which has deposited at DSMZ-Deutsche Sammlung von Mikroorganismen and Zellkulturen, with a deposit number DSM ACC3145.

A method for detecting osteoarthritis comprises steps of identifying a presence of type II collagen in a urine sample by containing the urine sample with the antibody as defined in claim 1 that specifically bind to unwound type II collagen, wherein epitope of the antibody has a sequence of: K-G-E-P-G-D-D-G-P-S-C (as set forth in SEQ ID NO. 1).

In the method for detecting osteoarthritis, a titer of the antibody is $5 \times 10^3$ to $1 \times 10^6$.

In the method for detecting osteoarthritis, the type II collagen in the urine sample is identified via western blot.

In the method for detecting osteoarthritis, further comprises steps of: dropping the urine sample on a slide; drying the urine sample on the slide; detecting the urine sample with the said antibody via western blot, with the antibody binding to unwind type II collagen in the urine sample; and identifying the presence of type II collagen sediment in the urine sample after contacting the urine sample with the said antibody.

In the method for detecting osteoarthritis, further comprise steps of: blotting the urine sample by using a western blotting reagent after the drying the urine sample on the slide, to fix protein of the urine sample on the slide; and detecting the urine sample with the antibody.

In the method for detecting osteoarthritis comprise steps of: fixing the said antibody on a test strip; detecting the urine sample with the said antibody on the test strip; and identifying the coloration on the test strip that positively relates to the progress of osteoarthritis.

In the method for detecting osteoarthritis, the type II collagen in the urine sample is identified via quartz crystal microbalance.

In the method for detecting osteoarthritis, the type II collagen in the urine sample is identified via ELISA.

Further scope of the applicability of the present invention will become apparent from the detailed description given hereinafter. However, it should be understood that the detailed description and specific examples, while indicating preferable embodiments of the invention, are given by way of illustration only, since various more will become apparent to those skilled in the art from this detailed description.

BRIEF DESCRIPTION OF THE DRAWINGS

The present invention will become more fully understood from the detailed description given herein below and the accompanying drawings which are given by way of illustration only, and thus are not limitative of the present invention, and wherein.

Figure 1:
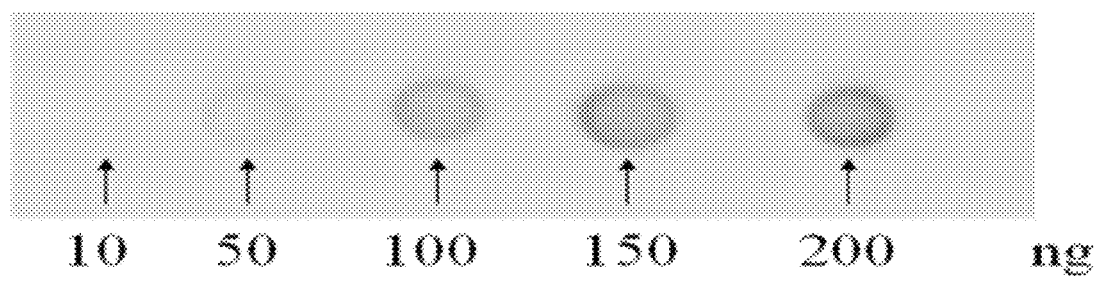
FIG. 1 is a western blot illustrating the sensitivity of an antibody in a preferable embodiment of the present invention.

All figures are drawn for ease of explaining the basic teachings of the present invention only; the extensions of the figures with respect to number, position, relationship, and dimensions of the parts to form the preferred embodiment will be explained or will be within the skill of the art after the following teachings of the present invention have been read and understood. Further, the exact dimensions and dimensional proportions conforming to specific force, weight, strength, and similar requirements will likewise be within the skill of the art after the following teachings of the present invention have been read and understood.

DETAILED DESCRIPTION OF THE INVENTION

A preferable embodiment of the present invention provides a hybridoma cell line which produces an antibody that binds to an epitope on unwound type II collagen peptides or fragments thereof. The hybridoma cell line of the preferable embodiment is obtained by interaperitoneally immunizing Balc/c mice to induce the Balc/c mice generating antibody, fusing spleen cells of immunized Balc/c mice with SP/o-Ag14 myeloma cells, and then screening and isolating a hybridoma cell line that produces an antibody which specifically binds to a neopeptide of type II collagen via enzyme-linked immunosorbent assay (ELISA). The antibody produced by obtained hybridoma cell line is apt to specifically bind to type II collagen peptides or fragments being a biomarker of osteoarthritis, wherein the hybridoma cell line has deposited under the terms of the Budapest Treaty in the biological resource center DSMZ-Deutsche Sammlung von Mikroorganismen and Zellkulturen on Oct. 6, 2011 with a DSMZ deposit number DSM ACC3145.

Specifically, the preferable embodiment of the present invention also provides a method for detecting osteoarthritis, which identifies a presence of type II collagen in a urine sample by containing the urine sample with an antibody that is produced by the said hybridoma cell line, for example via western blot, ELISA or quartz crystal microbalance (QCM), in order to achieving diagnosis of osteoarthritis at a high specificity and a high sensitivity.

In the present embodiment, a peptide comprising K-G-E-P-G-D-D-G-P-S-C (as set forth in SEQ ID NO. 1) is obtain via fluorenylmethyloxy-carbonyl(Fmoc)-solid phase peptide synthesis by using a Labortec SP 640 peptide synthesizer (Mission Biotech Ltd. Taipei, Taiwan). Also, an injection in a concentration of 50 mM, comprising 100 μg/ml immunogen (the said peptide comprising K-G-E-P-G-D-D-G-P-S-C) and complete Freund's adjuvant, is prepared, wherein a volume ratio between the said peptide and the complete Freund's adjuvant is 1:1.

Next, with reference to TABLE. 1, female and 6-8 weeks old Balc/c mice are purchased from National Applied Research Laboratories, and which are interaperitoneally immunized for the first time with 50 μg injection. After 3 weeks, four additional immunizations are also carried out intraperitoneally every two weeks, and last immunizations are carried out 10 days after the fifth immunization via intravenous injection through mouse tail. Then, 3 days after the last immunization, blood of the Balc/c mice are taken retro-orbitally to obtain mouse serum for confirming the presence of antibody therein.

TABLE 1

| Immunization of Balc/c Mice | | |
| --- | --- | --- |
| Injection | Time (days) | Dosage (μg) |
| $1^{st}$ | 0 | 50 |
| $2^{nd}$ | 21 | 50 |
| $3^{rd}$ | 35 | 50 |
| $4^{th}$ | 49 | 50 |
| $5^{th}$ | 63 | 50 |
| $6^{th}$ | 73 | 20 |

After the immunization, the Balc/c mice are killed to remove their spleens under a sterile environment, followed by pressing out the spleen cells, washing the spleen cells with RPMI-1640 medium for twice, and mixing with myeloma cells (SP/o-Ag14, ATCC CRL-1581™), wherein the myeloma cells is pre-cultured in RPMI-1640 medium comprising 5% FBS and L-glutamine till at $5\times10^6$ cell/ml.

Precisely, the spleen cells are mixed with myeloma cells in a ratio of 1:3 and centrifuged (10 minutes, 300 g, 4° C.), then washed again with RPMI-1640 medium and centrifuged at 400 g to decant supernatant thereof. After that, obtained cell sediments are loosened, and kept in a water bath for 1 minute after adding 1 ml polyethylene glycol-1500 (PEG-1500), followed by adding 5 ml RPMI-1640 medium at room temperature and centrifuging at 400 g for 10 minutes, with sedimentary cells being taken and cultured in HAT medium comprising 20% FBS. Since only hybridoma cell lines can survive in the HAT medium, it is capable of screening and isolating the hybridoma cell lines. The isolated hybridoma cell lines are further tested for specific antibody synthesis via western blot.

In the preferable embodiment of the present invention, one hybridoma cell line (DSM ACC3145) is obtained and is deposited at DSMZ-Deutsche Sammlung von Mikroorganismen and Zellkulturen, wherein antibody that produces by the hybridoma cell lines shows specifically affinity to unwound type II collagen peptides or fragments. The hybridoma cell line is further interaperitoneally injected to Balc/c mice (male, and 12 weeks old) that has 0.5 ml pristine (Sigma, St. Louis, Mo., USA) treatment in advance, and then, the Balc/c mice are killed to collect ascites thereof. The ascites of the Balc/c mice is purified by using an Econo-Pac® Protein A Kit (Bio-Rad, Hercules, Calif., USA) to obtain an antibody that specifically binds to an epitope on unwound type II collagen peptides or fragments, and the antibody (1 mg/ml) is diluted to $1:5\times10^3\sim1\times10^6$ in PBS buffer.

The antibody obtained from the preferable embodiment of the present invention can be applied to diagnosis of osteoarthritis, by identifying the presence of type II collagen in a sample through containing the urine sample with the said antibody that specifically bind to unwound type II collagen, and further detecting the antibody by HRP-linked anti-mouse IgG, IgA or IgM antibody. Preferably, the sample is urine sample.

With reference to FIG. 1, the sensitivity of the antibody is tested by dropping urine samples comprising various concentration (10, 50, 100, 150 and 200 ng) of protein on a nitrocellulose paper (or other substrates, such as slide), drying the urine samples on the nitrocellulose paper to fix the protein of the urine samples thereon, adding 5% skim milk (blocking reagent) on the nitrocellulose paper, with the 5% skim milk blocking the protein of the urine samples and waiting for 4 hours, washing the urine samples with PBS buffer for three times (5 minutes for each time), dropping the antibody (diluted 1:5000 in PBS buffer) on the nitrocellulose paper and waiting for 1 hour, with the antibody reacting with the protein of the samples, washing the urine samples with PBS buffer for another three times (10 minutes for each time), and finally dropping HRP-linked anti-mouse IgG (diluted 1:5000 in PBS buffer) on the nitrocellulose paper and waiting for 1 hour, and finally analyzing the nitrocellulose paper via Western Blotting Detection System (Millipore, Temecula, Calif., USA). Wherein, the urine samples are obtained from patients suffering from osteoarthritis, and the concentration of total protein in the urine samples are measured before the sensitivity test.

According to FIG. 1, it is noted that the antibody of the preferable embodiment in the present invention is capable of detecting the presence of type II collagen in a sample that only comprising 50 ng of total protein.

Figure 2A:
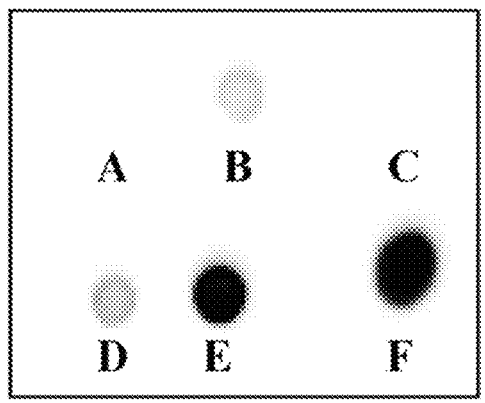
FIG. 2a is a western blot illustrating the detection of samples under a dilution rate of $1:5\times10^3$.
Figure 2B:
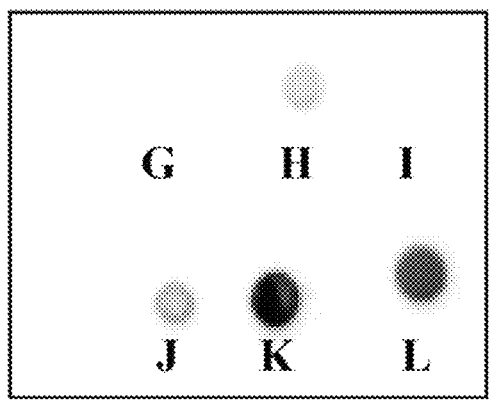
FIG. 2b is a western blot illustrating the detection of samples under a dilution rate of $1:4\times10^4$.
Figure 2C:
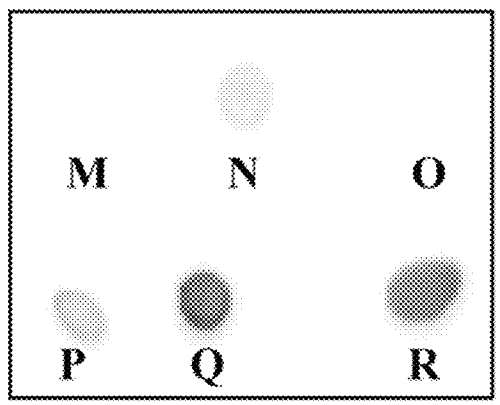
FIG. 2c is a western blot illustrating the detection of samples under a dilution rate of $1:1\times10^6$.

With reference to TABLE 2 and FIG. 2a~2c, the titer of the antibody is tested by serial diluting the antibody in PBS buffer (comprising 137 mM NaCl, 2.7 mM KCl, 10 mM $Na_2HPO_4$ and 2 mM $KH_2PO_4$), and using the antibody in various dilution rates (diluting $1:5\times10^3$, $1:4\times10^4$ and $1:1\times10^6$ in PBS buffer) to analyze urine samples (comprising 500 ng of total protein) that collected from various osteoarthritis patients or normal via western blot respectively.

TABLE 2

Groups Arrangement of the Titer Test

| Groups | Dilution Rates (in PBS) | Samples |
|---|---|---|
| A | $1:5 \times 10^3$ | $N^a 7$ |
| B | $1:4 \times 10^4$ | N2 |
| C | $1:1 \times 10^6$ | N10 |
| D | $1:5 \times 10^3$ | $S^b 44$ |
| E | $1:4 \times 10^4$ | S45 |
| F | $1:1 \times 10^6$ | S49 |
| G | $1:5 \times 10^3$ | N7 |
| H | $1:4 \times 10^4$ | N2 |
| I | $1:1 \times 10^6$ | N10 |
| J | $1:5 \times 10^3$ | N7 |
| K | $1:4 \times 10^4$ | N2 |
| L | $1:1 \times 10^6$ | N10 |
| M | $1:5 \times 10^3$ | S44 |
| N | $1:4 \times 10^4$ | S45 |
| O | $1:1 \times 10^6$ | S49 |
| P | $1:5 \times 10^3$ | S44 |
| Q | $1:4 \times 10^4$ | S45 |
| R | $1:1 \times 10^6$ | S49 |

[a] referring to Normal;
[b] referring to osteoarthritis patients

With datum of FIGS. 2a~2c, it is indicated that the titer of the antibody is in a range of $5\times10^3$ to $1\times10^6$, with the antibody specifically detecting the presence of type II collagen in a sample, even when diluting to $1:1\times10^6$. Hence, it is proved that the antibody of the preferable embodiment in the present invention is apt to be applied to the diagnosis of osteoarthritis.

In a preferable example of the present invention, the diagnosis of osteoarthritis can be also achieved by coating the antibody on a detection electrode of quartz crystal microbalance, contacting the detection electrode with a specimen, and identifying the binding between the antibody and the specimen by measuring changes in frequency.

Before the diagnosis, the detection electrode is prepared and washed by 0.5 M sulfuric acid, and succeeding, experimenting via cyclic voltammetry for 5 cycles (at 100 V/s), washing with deionized water and drying by nitrogen gas. As following, the detection electrode is further rinsed in 2.5 mM thioctic acid (TA), kept in a dark environment at room temperature for 24 hours, washed with alcohol, dried by nitrogen gas again, and then kept at room temperature till practical use. Before practical use, the detection electrode is activated by rinsing in 0.2 M 1-ethyl-3-(3-dimethylaminopropyl) carbodiimide hydrochloride (EDC) at room temperature for 3 hours, next, washed with alcohol and dried by nitrogen gas again. After that, 20 μl of the antibody (in a concentration of 1 mg/ml) of the preferable embodiment in the present invention is dropped on the detection electrode and kept at 4□, with the antibody connecting with a surface of the detection electrode and being coated thereon, followed by washing the detection electrode with PBS buffer, and blocking the detection electrode with 5% FBS for 1.5 hours. Finally, the detection electrode is washed with PBS buffer and dried by nitrogen gas.

Figure 3:
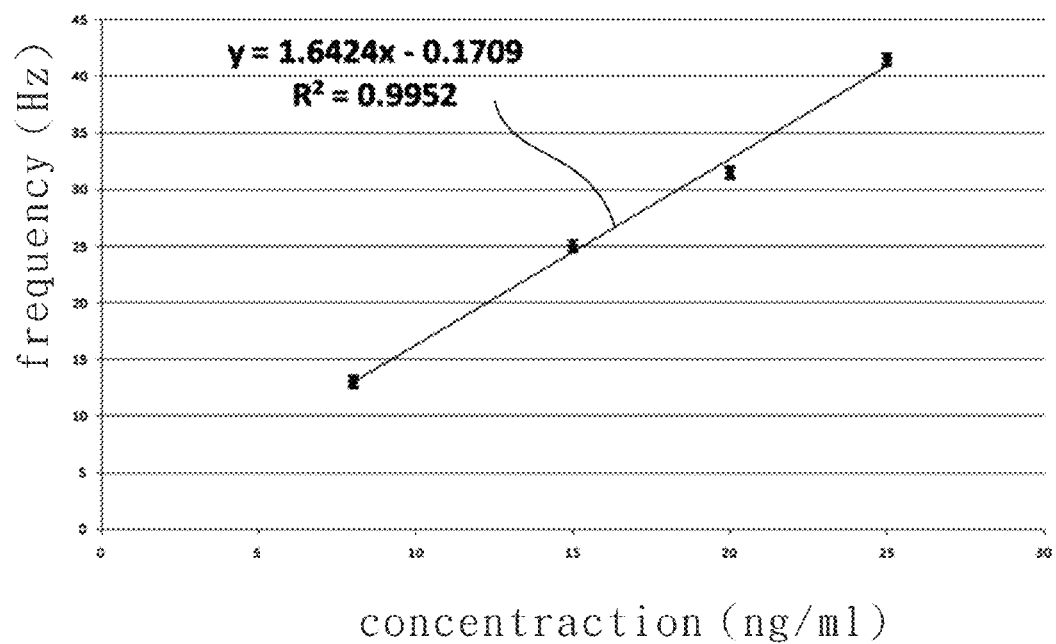
FIG. 3 is a line chart illustrating the data obtained from quartz crystal microbalance.

With reference to FIG. 3, the sample is detected by re-setting coated detection electrode at 10 MHz, rinse the coated detection electrode in PBS buffer (pH 7.4) till frequency turning stable, then sequentially rinse the coated detection electrode in various samples that comprising type II collagen peptides or fragments in different concentrations, and recording the changes in frequency in 25 minutes after rinse in each sample. Accordingly, a curvilinear regression of diagnosis will be obtained based on a relation between the changes in frequency and various concentrations of type II collagen peptides or fragments.

FIG. 3 shows that the changes in frequency positively relate to the concentrations of type II collagen peptides or fragments, wherein a linear regression line therein has an equation of the form $Y=1.6424X-0.1709$ ($R^2=0.9952$). It is shown that the detecting of osteoarthritis can be easy achieved by identifying the presence of type II collagen in a urine sample with a use of the antibody that specifically bind to unwound type II collagen in the present invention via QCM.

Through the present invention, the hybridoma cell line that produces the antibody which specifically binds to a neopeptide of type II collagen comprising: K-G-E-P-G-D-D-G-P-S-C (as set forth in SEQ ID NO. 1) is obtained. With antibody produced by the hybridoma cell line, it is sufficient to identify the presence of type II collagen in a urine sample at a high sensitivity and a high specificity. Also, the antibody can be further applied to a method for detecting osteoarthritis, to specifically identify the presence of type II collagen in a urine sample by containing the urine sample with the said antibody, with the said antibody specifically binding and indicating unwound type II collagen in various samples, particularly to urine sample.

With such performance, a detection kit of osteoarthritis can be also developed, and comprises a test strip coated with the said antibody, with the test strip rapidly and specifically detect the presence of unwound type II collagen in various samples (such as urine sample), and with the coloration degree determining the degeneration of cartilages. Therefore, the diagnosis of degeneration of cartilages can be fast and easy achieved at home through a low-cost and convenient process, so as to reduce the incidence to osteoarthritis.

Although the invention has been described in detail with reference to its presently preferred embodiment, it will be understood by one of ordinary skill in the art that various modifications can be made without departing from the spirit and the scope of the invention, as set forth in the appended claims.

What is claimed is:

1. A method for detecting osteoarthritis, comprising the steps of:
   identifying the presence of unwound type II collagen or fragments thereof in a urine sample by contacting the urine sample with an antibody produced by the hybridoma cell line deposited at DSMZ-Deutsche Sammlung von Mikroorganismen and Zellkulturen with deposit number DSM ACC3145; and
   detecting binding by the antibody, wherein the presence of unwound type II collagen or fragments thereof in the urine sample indicates osteoarthritis.

2. The method of claim 1, wherein the antibody is used at a titer of $5 \times 10^3$ to $1 \times 10^6$.

3. The method of claim 1, wherein the unwound type II collagen or fragments thereof in the urine sample are identified via western blot.

4. The method of claim 3, further comprising the steps of:
   dropping the urine sample on a slide; and
   drying the urine sample on the slide, wherein the presence of the unwound type II collagen or fragments thereof in the urine sample are identified after contacting the urine sample with the antibody.

5. The method of claim 4, further comprising the step of blotting the urine sample using a western blotting reagent after the drying of the urine sample on the slide.

6. The method of claim 1, wherein the antibody is fixed on a test strip.

7. The method of claim 1, wherein the unwound type II collagen or fragments thereof in the urine sample are identified via quartz crystal microbalance.

8. The method of claim 1, wherein the unwound type II collagen or fragments thereof in the urine sample are identified via ELISA.

* * * * *

```
                        SEQUENCE LISTING

<160> NUMBER OF SEQ ID NOS: 1

<210> SEQ ID NO 1
<211> LENGTH: 11
<212> TYPE: PRT
<213> ORGANISM: Artificial Sequence
<220> FEATURE:
<223> OTHER INFORMATION: synthesizing partial fragment of type II
      collagen

<400> SEQUENCE: 1

Lys Gly Glu Pro Gly Asp Asp Gly Pro Ser Cys
1               5                   10
```